(12) United States Patent
Johnson et al.

(10) Patent No.: US 6,203,572 B1
(45) Date of Patent: Mar. 20, 2001

(54) DEVICE AND METHOD FOR LIGAMENT RECONSTRUCTION

(75) Inventors: Donald H. Johnson, Nepaan (CA); Donald A. Powers, Palm Harbor, FL (US)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 09/247,724

(22) Filed: Feb. 9, 1999

(51) Int. Cl.$^7$ .............................. A61F 2/68; A61B 17/00
(52) U.S. Cl. ..................... 623/13.15; 606/99; 606/108
(58) Field of Search .................. 623/13.11, 13.13, 623/13.15; 606/86, 99, 108, 148, 151

(56) References Cited

U.S. PATENT DOCUMENTS

| | | |
|---|---|---|
| 869,686 | 10/1907 | Bauno . |
| 2,442,176 | 5/1948 | Orr et al. . |
| 2,688,961 | 9/1954 | Thomas . |
| 3,176,316 | 4/1965 | Bodell . |
| 4,584,722 | 4/1986 | Levy et al. . |
| 4,668,233 | 5/1987 | Seedhom et al. . |
| 4,775,380 | 10/1988 | Seedhom et al. . |
| 4,790,850 | 12/1988 | Dunn et al. . |
| 4,834,755 | 5/1989 | Silvestrini et al. . |
| 4,917,699 | 4/1990 | Chervitz . |
| 4,917,700 | 4/1990 | Aikins . |
| 4,932,972 | 6/1990 | Dunn et al. . |
| 4,946,377 | 8/1990 | Kovach . |
| 4,990,158 | 2/1991 | Kaplan et al. . |
| 4,997,434 | 3/1991 | Seedhom et al. . |
| 5,116,373 | 5/1992 | Jokob et al. . |
| 5,147,400 | 9/1992 | Kaplan et al. . |
| 5,171,274 | 12/1992 | Fluckiger et al. . |
| 5,217,495 | 6/1993 | Kaplan et al. . |
| 5,451,203 | 9/1995 | Lamb . |
| 5,456,721 | 10/1995 | Legrand . |
| 5,549,676 | 8/1996 | Johnson . |
| 5,571,139 | 11/1996 | Jenkins, Jr. . |

OTHER PUBLICATIONS

Linvatec Concept Arthroscopy, "The Paramax ACL Guide System Surgical Technique", 28 pages.

*Primary Examiner*—David J. Isabella
(74) *Attorney, Agent, or Firm*—Duane, Morris & Heckscher LLP

(57) ABSTRACT

A device is disclosed for delivery of grafts such as, for example, semitendinosus and/or gracilis tendons for reconstructive surgery. The device is a woven structure whose diameter is reduced when placed in tension. It has a tapering end and an open end. A suture is looped within the device so that the loop extends from the open end to receive the folded graft. The suture is pulled to insert the graft into the device. The graft, after folding and being pulled into the device, may have sutures extending out of one end as an optional feature to facilitate subsequent fixation. The sutures extending through the tapered end are pulled, tightening the device around the graft while pulling the device with the graft inside through the bone tunnels such as, for example, tibial and femoral tunnels. The narrow tapering end traps the graft as the device tightens around the graft for insertion into the tunnels. The suture ends are threaded through a conventional suture-passing device so that the suture can pass through the tunnel and out through a small opening in the lateral femur. The suture pulls the device and the graft into the bone tunnels. The device remains in place and is absorbed due to its construction of compatible suture and the graft is secured in a conventional manner with, for example, bioabsorbable interference screws.

25 Claims, 4 Drawing Sheets

DEVICE AND METHOD FOR LIGAMENT RECONSTRUCTION

FIELD OF THE INVENTION

This invention relates to appliances used to capture and insert a soft tissue graft during an arthroscopic reconstruction, and more specifically for insertion into a tibial and femoral tunnel during an anterior cruciate ligament (ACL) or posterior cruciate ligament (PCL) reconstruction.

Background of the Invention

Soft tissue grafts are used frequently. In order to insert the soft tissue graft into the joint, substantial time is required to prepare the graft by whipstitching it. Such known procedures normally take approximately 10 minutes for the suturing of the graft prior to insertion. Other known surgical techniques for ACL reconstruction using a graft passer are described in detail in the Paramax ACL Guide System from Linvatec Corporation. The same procedure is also described in another Linvatec publication entitled "Arthroscopic Anterior Cruciate Ligament Reconstruction." Numerous patents have disclosed reconstructive ACL surgical techniques involving prosthetic ligament assemblies. Typical of these patents are U.S. Pat. Nos. 4,790,850; 4,775,380; 4,668,233; 5,171,274; 5,456,721; 4,917,700; 4,917,699; 5,549,676; 5,116,373; and 4,932,972. Other patents disclosed replacements for biological tissue to function in parallel or in place of biological tissue for temporary or permanent use. Typical of these patents are U.S. Pat. Nos. 4,946,377; 5,217,495; 5,147,400; 4,990,158; 3,176,316; and 4,834,755.

Braided or woven tubular designs which have application as novelty toys and are commonly known as "finger traps" are disclosed in U.S. Pat. Nos. 869,683; 2,442,176; and 2,688,961. U.S. Pat. No. 5,571,139 shows a bi-directional suture anchor. U.S. Pat. No. 5,451,203 shows a traction mechanism in the form of a finger trap which can be used as a traction device for implantation of prosthetic meniscus in a knee when placed in tension and the device can be removed with a release loop which places the finger trap in compression to increase its diameter for disengagement.

It is an object of the invention to eliminate the need for whipstitching which had previously been done to reduce the dimension of a 4-bundle semitendinosus graft so that it could be pulled into the tunnel and fixed with interference screws. The objective of the invention is to use the finger trap tubular structure to place the sutures on the surface of the graft to hold multiple bundles of the graft together as a quicker and easier option than suturing them together with whipstitching using multiple sutures.

Another objective of the invention is to render optional the suturing of the soft tissue graft in order to be able to insert it into the femoral and tibial tunnels, for example, or into tunnels for any other joint. Another objective of the invention is to decrease the overall time required for ACL reconstruction or other types of reconstruction using this procedure. Another objective is to make the device absorbable once it has served its function of placement of the soft tissue graft in the tunnels for fixation by, for example, screw insertion.

Another object of the present invention is to provide a device and method which is economical and simple to use in a variety of reconstructive surgeries.

SUMMARY OF THE INVENTION

A device is disclosed for delivery of grafts such as, for example, semitendinosus and/or gracilis tendons for reconstructive surgery. The device is a woven structure whose diameter is reduced when placed in tension. It has a tapering end and an open end. A suture is looped within the device so that the loop extends from the open end to receive the folded graft. The suture is pulled to insert the graft into the device. The graft, after folding and being pulled into the device, may have sutures extending out of one end as an optional feature to facilitate subsequent fixation. The sutures extending through the tapered end are pulled, tightening the device around the graft while pulling the device with the graft inside through the bone tunnels such as, for example, tibial and femoral tunnels. The narrow tapering end traps the graft as the device tightens around the graft for insertion into the tunnels. The suture ends are threaded through a conventional suture-passing device so that the suture can pass through the tunnel and out through a small opening in the lateral femur. The suture pulls the device and the graft into the bone tunnels. The device remains in place and is absorbed due to its construction of compatible suture and the graft is secured in a conventional manner with, for example, bioabsorbable interference screws.

DETAILED DESCRIPTION OF THE PREFERRED EMBODIMENT

Figure 1:
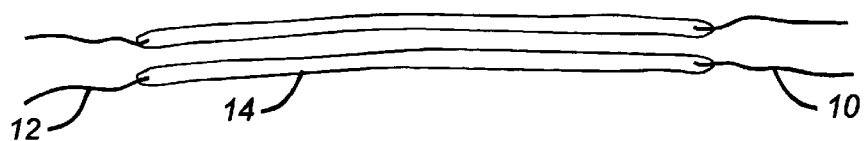
FIG. 1 illustrates the graft to be used with optional sutures at opposite ends.
Figure 2:
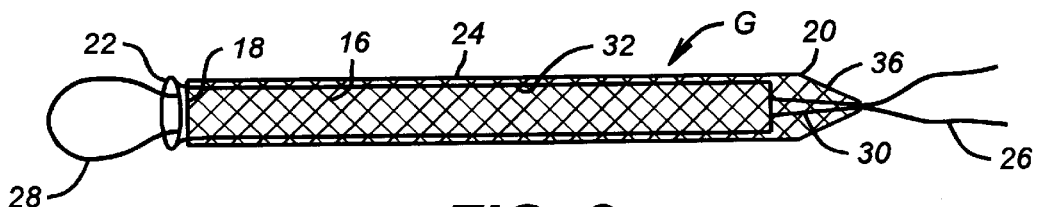
FIG. 2 illustrates the device with the suture looped through and extending out of its open end to receive the graft and with an optional, tubular introducer in place within the device.

FIG. 1 illustrates harvested autologous soft tissue graft which has been harvested in the usual fashion. Sutures 10 and 12 can be applied to gain tension during the harvest of, for example, the semitendinosus and/or gracilis tendons 14. The apparatus G of the present invention is made of biocompatible sutures in a woven pattern 16, creating a tubular shape or structure with an open end 18 and a tapered end 20. An optional introducer 22 may be inserted into the apparatus G which is built akin to a finger trap. For the purposes of this application, the apparatus G will be referred to as a graft trap.

Figure 4:
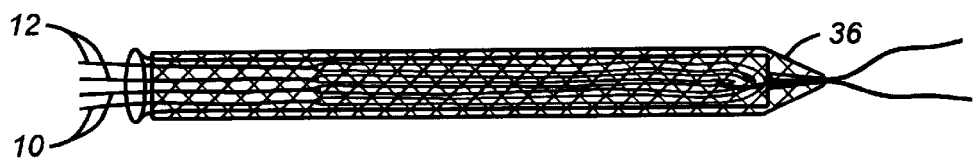
FIG. 4 shows the folded graft pulled into the device with sutures extending from the graft out of the open end of the device.

The optional introducer 22 keeps the graft trap 24 open internally so that a suture 26 can be inserted through the tapered end 20 and out the open end 18 to create a loop 28 outside the open end 18 to receive the graft 14, as will be described below. The nature of the graft trap 24 is that under tension, its length increases and its diameter decreases. The reverse occurs under compression. At the tapered end 20, there is a narrow opening 30 sufficient to allow suture 26 to pass. The internal passage 32 necks down at narrow passage 30 such that when the graft segments 14 are inserted into the graft trap 24, their forward motion will stop upon encountering the end 34 of internal passage 32, as shown in FIG. 4.

Figure 11:
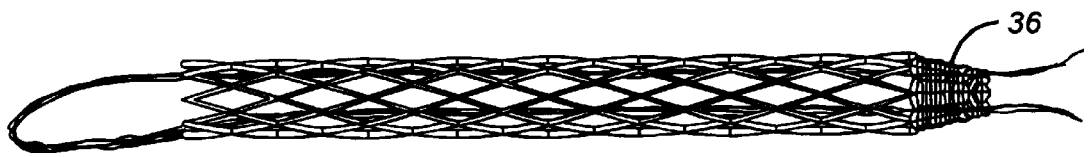
FIG. 11 is a section view of the device.

The tapered end 20 has a taper 36 which, in effect, creates the narrow passage 30, as shown in FIG. 11. Thus, for example, for a graft trap 24 that is approximately 4.4" long, the outer diameter is approximately 0.433" while the opening of narrow passage 30 is approximately 0.157".

Figure 3:
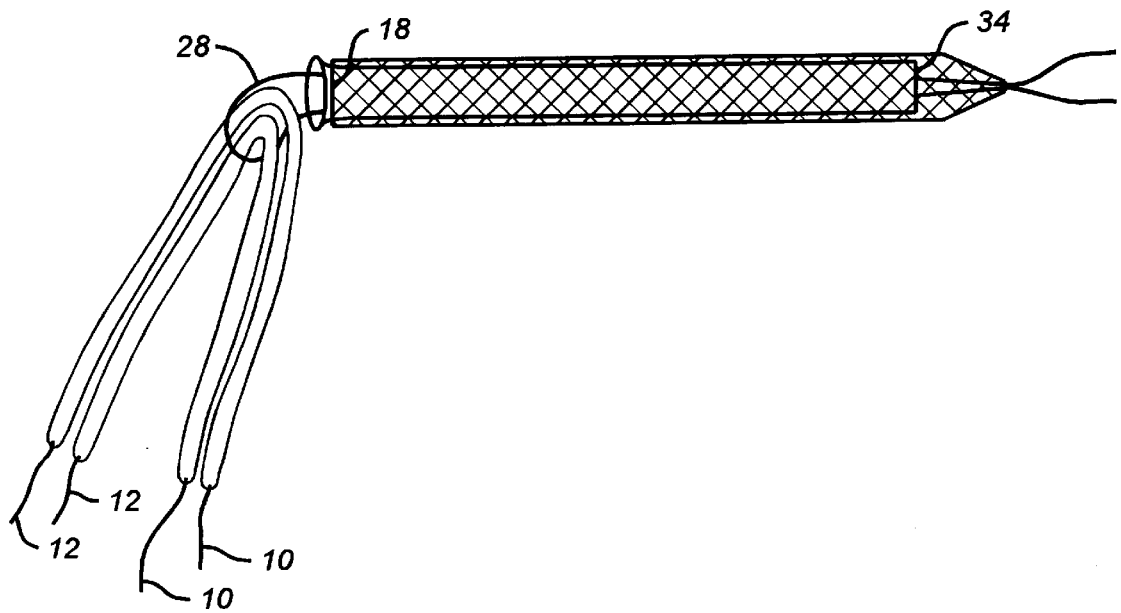
FIG. 3 shows the graft folded and inserted through the loop extending from the open end of the device.
Figure 5:
FIG. 5 is the view of FIG. 4 with the optional introducer removed from the device, with the device ready to be passed through the tibial and femoral tunnels.

Referring to FIG. 3, the graft 14 is folded, preferably in half at least twice; however, other folding techniques can be used without departing from the spirit of the invention. FIG. 3 illustrates the grafts folded over in half once and inserted through loop 28. In FIG. 3, four individual grafts 14 are used and, hence, two sets of sutures 10 and 12 extend from the open end 18 of the graft trap 24. Again, other folding techniques can be used without departing from the spirit of the invention. The suture 26 is pulled when the grafts 14 are looped through suture loop 28. As a result, the grafts 14 are pulled into passage 32 until they encounter the taper 36 which has narrow passage 30. At this time, the grafts 14 are fully inserted into the graft trap 24 and the introducer 22, if it is used, may be removed. The sutures 10 and 12 extend out the open end 18 of the graft trap 24. FIG. 5 shows the introducer 22 removed, with the grafts 14 pulled up into the taper 36.

Figure 7:
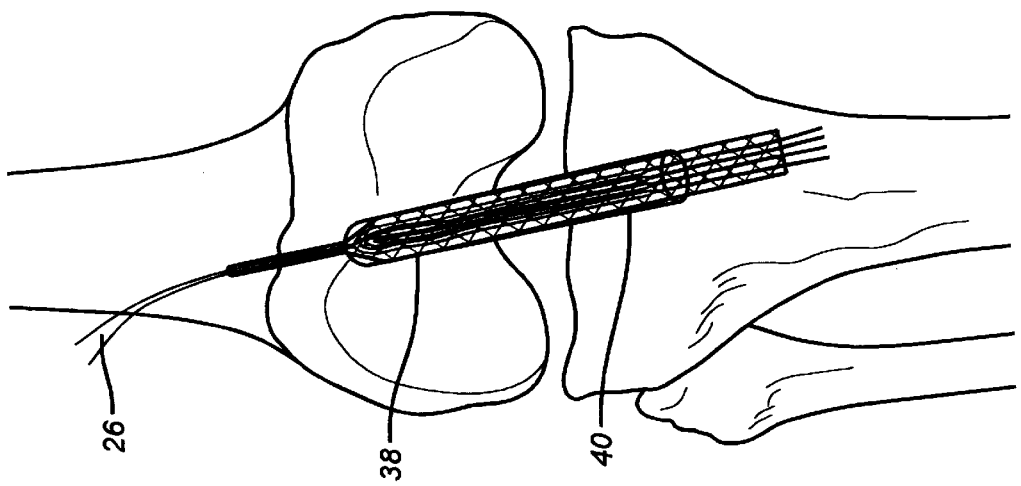
FIG. 7 shows the device fully pulled into the femoral tunnel.
Figure 6:
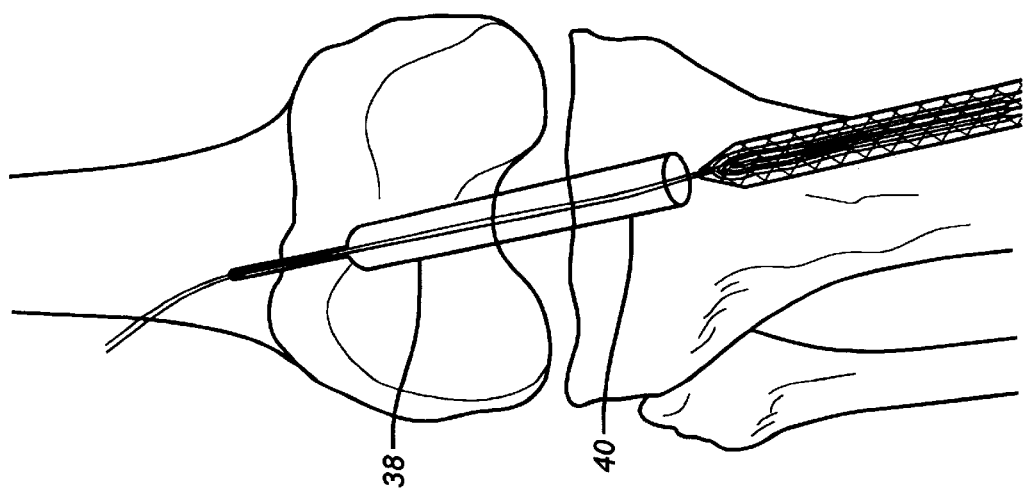
FIG. 6 shows the sutures pulling the device by its narrow end into the tibial tunnel.

FIG. 6 shows the suture 26 fed through a graft passing guide or a two-pin passer (not shown) and extending out through the femoral tunnel 38 after being pulled through the tibial tunnel 40. Tension is maintained on the femoral side by pulling on the leading suture 26. Tension is maintained on the tibial side by holding either the sutures 10 and 12 or the graft trap 24 itself. The trap 24 is pulled tight before insertion into tunnels 40 and 38. The act of pulling through tunnels 40 and 38 maintains the tension on trap 24 which, in turn, holds the grafts 14 compressed. FIG. 6 thus shows the pulling of the graft trap 24 in through the tibial tunnel 40, while FIG. 7 shows the graft trap 24 fully pulled into the femoral tunnel 38. As shown in FIG. 7, parts of the graft trap 24 extend out of the tibial tunnel 40 so that they may be grasped in conjunction with an opposing pull on suture 26 to put tension on the graft trap 24. The placement of tension on the graft trap 24 reduces its overall diameter while extending its length, as previously mentioned. Thus, the graft trap 24 serves the same function as whipstitching but bundles the graft 14 together much more quickly and efficiently. Ultimately, the sutures which make up the graft trap 24 are bioabsorbed.

Figure 9:
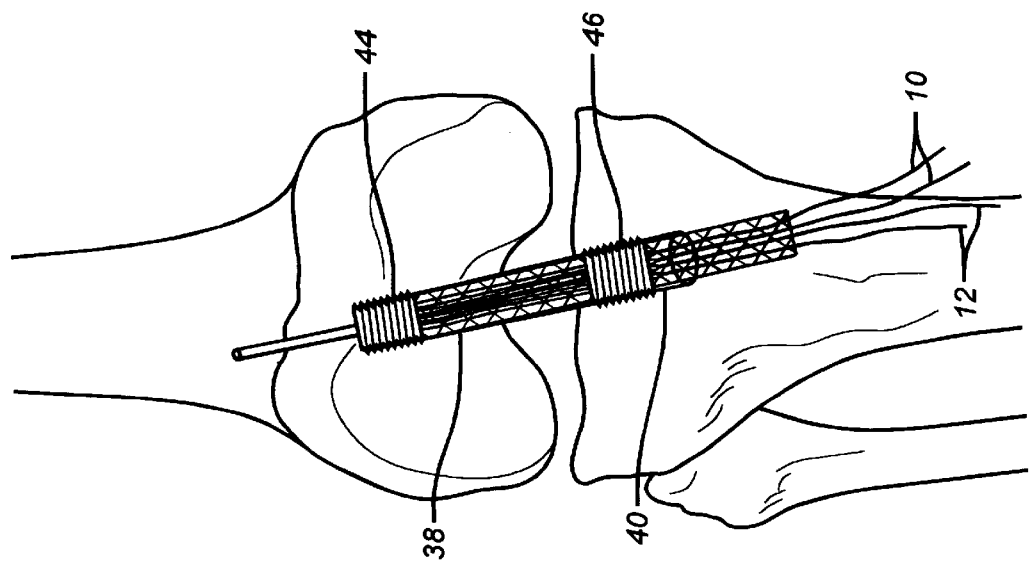
FIG. 9 shows the insertion of an interference screw to fixate the device in the tibial tunnel.
Figure 8:
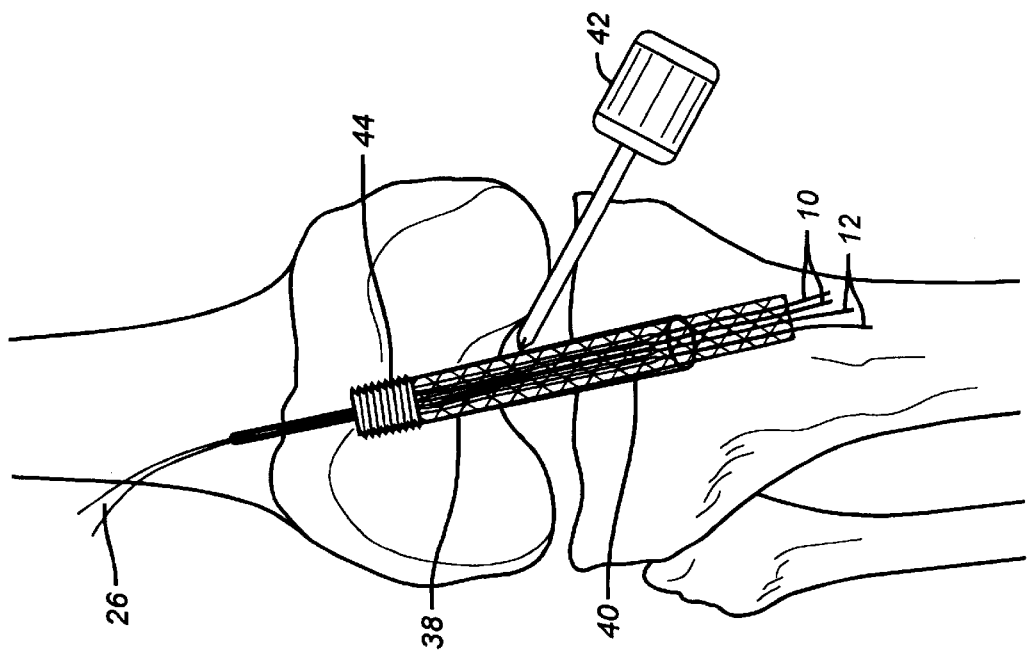
FIG. 8 shows the insertion of an interference screw to fixate the device in the femoral tunnel.
Figure 10:
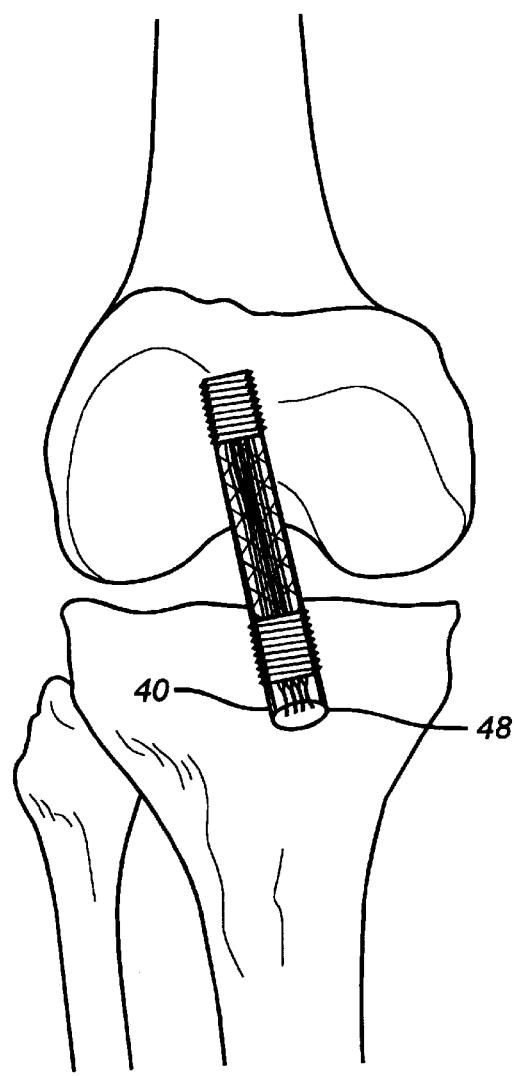
FIG. 10 shows the secured soft tissue graft in the tibial and femoral tunnels at the conclusion of the procedure.

FIGS. 8–10 illustrate the concluding steps of the procedure once the graft trap 24 has been fully pulled into the femoral tunnel 38. At this time, as shown in FIG. 8, with tension maintained on sutures 26 which extend through the femoral tunnel 38, a screwdriver 42 is used to insert an interference screw 44 into the femoral tunnel 38 to fixate the graft 14 in the femoral tunnel 38. With the screw 44 inserted, the graft trap 24 can be pulled to put the assembly under tension while an interference screw 46 is inserted in the tibial tunnel 40 in the same manner as previously described for screw 44. It should be noted that tension can be maintained on the grafts 14 by pulling on sutures 10 and 12 as an alternate to pulling on the graft trap 24 with the screw 44 in place. It is preferred that the interference screw 46 be installed in a known manner when the graft trap 24 and the grafts 14 are in tension. Referring to FIG. 10, the excess material from the graft trap 24, as well as sutures 10 and 12, are cut off at the opening 48 of the tibial tunnel 40.

Those skilled in the art can see that the use of the graft trap 24 with a taper 36 allows for simple insertion of the graft 14, which is preferably folded in equal lengths prior to engagement with loop 28. Once the suture 26 pulls the grafts 14 fully within the graft trap 24, any tension maintained on the graft trap 24 compacts the grafts 14, while at the same time the taper 36, with its narrow opening 30, maintains the grafts 14 within the passage 32 of the graft trap 24. The grafts 14 are fed through the tibial and femoral tunnels while the graft trap 24 is in tension, thus ensuring that the grafts 14 are properly gripped and fully compressed to aid in the insertion into the tibial and femoral tunnels. Initial insertion allows for tension to be applied to the grafts 14 simply by a pulling force on the suture 26 for insertion into the tibial and femoral tunnels 40 and 38, respectively, as shown in FIG. 6. Tension can be maintained for the placement of screw 46 in a known manner by a pull on the graft trap 24 or the extending sutures 10 and 12 which are connected to the grafts 14. The knee is flexed to 120° for insertion of the femoral interference screw 44. The knee is flexed to the 30° position for the insertion of the tibial interference screw 46.

In the preferred embodiment, the grafts 14 are folded in half twice to produce the standard "4 bundles." The graft is then folded over the suture loop 28. Sutures 26 can be used to fully tension the graft trap 24 while holding its open end so as to fully tighten the graft trap 24 around the graft 14. The graft insertion and the interference screw insertion are completed in comparable times to techniques in the past where the graft is first sutured with whipsttching. However, the main difference is that the preparation of the graft using the graft trap 24 can be accomplished in about 45 seconds after the graft is harvested, as opposed to a procedure using whipstitching which would take in excess of 10 minutes. The material for the graft trap 24 is preferably a compatible suture woven into a tubular structure which is eventually absorbed.

Although a technique has been described for ACL reconstruction, other reconstructive techniques for different joints can be accomplished using the graft trap and the method described herein. While certain examples of graft material have been provided as preferred, other graft materials, both natural and manmade, can be employed in conjunction with the graft trap 24 without departing from the spirit of the invention.

The foregoing disclosure and description of the invention are illustrative and explanatory thereof, and various changes in the size, shape and materials, as well as in the details of the illustrated construction, may be made without departing from the spirit of the invention from the spirit of the invention.

What is claimed is:

1. A graft-delivery device for retaining a graft and delivering it to a patient's bone structure through a tunnel therein, comprising:

an elongated biocompatible tubular structure having an axis, a proximal end, a distal end and a passage therethrough adapted to axially receive an elongated graft through said distal end, said structure having a cross sectional area, which upon application of axially aligned tension varies in diameter such that, said tubular structure reduces its cross sectional area to thereby frictionally engage the graft and enable said graft to be pulled into said passage by the application to said structure of axial force.

2. The device of claim 1, wherein:
said tubular structure comprises a taper to retain a graft inserted therein.

3. The device of claim 2, wherein:
said tubular structure is formed of a material used to make sutures.

4. The device of claim 3, wherein:
said tubular structure comprises a woven structure.

5. A graft delivery device for a patient's bone structure through a tunnel therein, comprising:
a biocompatible tubular structure adapted to receive a graft, said structure having a cross sectional area, whereupon application of tension, said tubular structure reduces its cross sectional area to retain the graft and for application of tensile force to the graft as it is fixated;
said tubular structure comprises a taper to retain a graft inserted therein;
said tubular structure is formed of a material used to make sutures;
said tubular structure comprises a woven structure;
a suture folded over and inserted through said taper to extend as a loop out of the opposite end from said taper, said suture movably mounted with respect to said taper for pulling said loop into said tubular structure whereupon when the graft is inserted through said loop, said suture can be used to pull it toward said taper.

6. The device of claim 5, further comprising:
a tubular introducer extending into said tubular structure to facilitate insertion of the graft in said tubular structure.

7. A graft delivery device for a patient's bone structure through a tunnel therein, comprising;
a biocompatible tubular structure adapted to receive a graft advanced therethrough, said structure having a cross sectional area, whereupon application of tension, said tubular structure reduces its cross sectional area to retain the graft and for application of tensile force to the graft as it is fixated;
said tubular structure comprises a taper to retain a graft inserted therein;
a passage defined by said tubular structure;
said taper comprises an opening smaller than said passage;
said tubular structure further comprises a suture folded over and inserted through said taper to extend as a loop out the opposite end, whereupon when the graft is inserted through said loop, said suture can be used to pull it toward said taper.

8. The device of claim 7, wherein:
when said suture advances the graft to said taper said taper prevents further advancement of said graft, whereupon tension in said tubular structure results from pulling said suture while holding the end of said tubular structure opposite said taper.

9. The device of claim 8, further comprising:
a first fixation device to affix said tubular structure to the patient's bone structure;
said suture maintains tension on said tubular structure at the location of said taper as said tubular structure is fixated by said first fixation device to the patient's bone structure.

10. The device of claim 9, further comprising:
a second fixation device;
said tubular structure maintains a compressive force on the graft when pulled after fixating said tapered region with said first fixation device so as to allow fixation of its opposite end in an adjoining bone structure with said second fixation device.

11. The device of claim 10, wherein:
said suture pulls said tubular structure through a tunnel in the patient's bone structure and causes said tubular to collapse around said graft to apply a compressive force to the graft.

12. A method of reconstructive joint surgery using a graft; comprising:
inserting the graft into a flexible biocompatible tubular structure having a passage therethrough;
applying a tensile load to said tubular structure;
compressing said graft in said tubular structure due to said tensile load;
inserting said tubular structure and graft into a desired position in the joint using tension applied to said tubular structure;
fixating said graft mounted in said tubular structure in said position while under tension applied to said tubular structure.

13. The method of claim 12, further comprising:
providing a taper in said tubular structure to retain said graft.

14. The method of claim 13, further comprising:
inserting a suture through said taper until it exits the opposite end of said tubular structure.

15. A method of reconstructive joint surgery using a graft; comprising:
inserting the graft into a flexible biocompatible tubular structure;
applying a tensile load to said tubular structure;
compressing said graft in said tubular structure due to said tensile load;
inserting said tubular structure and graft into a desired position in the joint;
fixating said graft mounted in said tubular structure in said position;
providing a taper in said tubular structure to retain said graft;
inserting a suture through said taper until it exits the opposite end of said tubular structure;
looping said suture at said opposite end.

16. The method of claim 14, further comprising:
attaching said graft to said suture;
pulling said suture and graft into said tubular structure;
using said taper to act as a travel stop for said graft.

17. The method of claim 15, further comprising:
folding said graft through said looped suture;
pulling said looped suture and folded graft into said tubular structure;
using said taper to act as a travel stop for said graft.

18. The method of claim 17, further comprising:
using said suture extending from said taper to pull the compressed graft through bone tunnels which span a joint.

19. The method of claim 18, further comprising:
using said suture which extends from said taper to maintain tension on said taper;

securing said taper in one of the bone tunnels which span the joint.

20. The method of claim 19, further comprising:

pulling on said tubular structure with said taper fixated;

fixating the opposite end from said taper while maintaining said tension.

21. The method of claim 12, further comprising:

forming said tubular structure from a material used to make sutures.

22. The method of claim 21, further comprising:

using a woven pattern of said suture which reduces diameter under tension.

23. A method of reconstructive joint surgery using a graft, comprising:

inserting the graft into a flexible biocompatible tubular structure;

applying a tensile load to said tubular structure;

compressing said graft in said tubular structure due to said tensile load;

inserting said tubular structure and graft into a desired position in the joint;

fixating said graft mounted in said tubular structure in said position;

forming said tubular structure from a material used to make sutures;

using a woven pattern which reduces diameter under tension;

folding said graft in equal lengths at least once prior to insertion into said tubular structure.

24. The method of claim 12, further comprising:

providing bone tunnels in a patient's femur and tibia;

positioning said graft compressed by said tubular structure into bone tunnels in a patient's femur and tibia.

25. A graft-delivery device, comprising:

a biocompatible tubular structure having a diameter and adapted to receive a graft through a passage extending therethrough, said tubular structure further comprising means for reducing the diameter of said tubular structure in order to frictionally retain said graft upon application of a longitudinally directed force to said tubular structure said passage constricted to stop advancement of said graft such that tensile force on said graft advances the tubular structure for fixation.

* * * * *